United States Patent [19]

Maranhão

[11] Patent Number: 5,578,583
[45] Date of Patent: Nov. 26, 1996

[54] MICROEMULSIONS USED AS VEHICLES FOR CARRYING CHEMOTHERAPEUTIC AGENTS TO NEOPLASTIC CELLS

[75] Inventor: Raul C. Maranhão, São Paulo, Brazil

[73] Assignee: Fundacão E. J. Zerbini, São Paulo, Brazil

[21] Appl. No.: 388,148

[22] Filed: Feb. 13, 1995

Related U.S. Application Data

[63] Continuation of Ser. No. 42,105, Apr. 1, 1993, abandoned.

[51] Int. Cl.$^6$ .......... A61K 31/175; A61K 31/70; B01J 13/00
[52] U.S. Cl. .......... 514/49; 252/312; 514/589; 514/908; 514/938
[58] Field of Search .......... 252/312; 428/402.2; 514/908, 938, 49, 589; 530/359, 388.25, 389.3, 388.7, 388.8, 389.6, 387.7

[56] References Cited

U.S. PATENT DOCUMENTS

| | | | |
|---|---|---|---|
| 3,992,513 | 11/1976 | Petkau et al. | 252/312 X |
| 4,073,943 | 2/1978 | Wretlind et al. | 514/938 X |
| 4,298,594 | 11/1981 | Sears et al. | 424/450 |
| 4,769,250 | 9/1988 | Forssen | 424/450 |
| 4,797,285 | 1/1989 | Barenholz et al. | 424/450 |
| 4,906,477 | 3/1990 | Kurono et al. | 424/450 |
| 4,963,363 | 10/1990 | Forssen | 424/450 |
| 4,970,144 | 11/1990 | Fareed et al. | 530/387 X |
| 4,975,528 | 12/1990 | Kaminski et al. | 530/359 |
| 5,004,756 | 4/1991 | Ogawa et al. | 514/938 X |
| 5,089,602 | 2/1992 | Isliker et al. | 530/359 |
| 5,152,923 | 10/1992 | Weder et al. | 252/312 |
| 5,369,009 | 11/1994 | Arceci et al. | 530/388.8 X |
| 5,407,836 | 4/1995 | Ziegenhorn et al. | 530/389.3 X |

OTHER PUBLICATIONS

Ginsburg et al., :"Microemulsions of Phospholipids and Cholesterol Esters", *J. Biol. Chem.*, 257:8216–8227, Jul. 25, 1982.

*Martindale–The Extra Pharmacopoeia*–28th Edition, Edited by James E. F. Reynolds, The Pharmaceutical Press, London (1982), pp. 195, 203 & 204.

Reisinger et al., :"Phospholipid/Cholesterol Ester Microemulsions Containing Unesterified Cholesterol . . . ", *J. Lipid Res.* 31:849–858, 1990.

*Primary Examiner*—Richard D. Lovering
*Attorney, Agent, or Firm*—Darby & Darby, P.C.

[57] ABSTRACT

Microemulsions, similar in chemical composition to the lipid portion of low density lipoprotein (LDL), but not containing the protein portion, can be used as vehicles for the delivery of chemotherapeutic or diagnostic agents to neoplastic cells, while avoiding normal cells. When these artificial microemulsion particles are injected in the bloodstream or incubated with plasma, they incorporate plasma apolipoproteins on to their surface. The microemulsions can then be incorporated into cells via receptors for LOL and deliver molecules which are incorporated in the core or at the surface of the microemulsion.

4 Claims, No Drawings

MICROEMULSIONS USED AS VEHICLES FOR CARRYING CHEMOTHERAPEUTIC AGENTS TO NEOPLASTIC CELLS

This is continuation of application Ser. No. 08/042,105, filed Apr. 1, 1993 abandoned.

FIELD OF THE INVENTION

The microemulsions, which are similar to the lipidic composition of the LDL, but without protein, can serve as vehicles for carrying chemotherapeutic agents specifically to the neoplastic cells, avoiding the normal cells.

BACKGROUND OF THE INVENTION

The microemulsions, with a chemical composition similar to that of the LDL (low density, lipoprotein) and without protein, can join the LDL specific receptors, which exist in most tissues of the body. These microemulsions have a hydrophobic nucleus, consisting of cholesterol esters, though it can also present triglycerides and, surrounding the nucleus, there is a monolayer of phospholipides, though free cholesterol can also be found. The microemulsions are prepared by exposing to ultrasound the lipids that form these microemulsions, in an aqueous medium, and can be purified by various methods, such as ultracentrifugation or gel filtration. The lipidic mixture can also be emulsified by passing through the press of French. The microemulsions, when ejected in the blood stream, incorporate to their surfaces the apolipoprotein E (apo R), which exists in the plasma, associated to the plasmatic lipoproteins or in the free form. Thus, the apolipoprotein E serves as a linking element between the particles of the microemulsion and the LDL receptors, which recognize the apo E. It is known in the literature that the LDL receptors are highly increased in several lineages of neoplastic cells. Anticancer drugs can be incorporated to the LDL, reaching high concentrations in the neoplastic cells that have an increased expression of the receptors, and avoiding the normal cells, whose LDL receptors are comparatively reduced. It is therefore possible to send drugs specifically to the endoplastic tissues, avoiding the toxic effects of these drugs on the normal tissues and organs. The plasmatic LDL are not feasible for the treatment, due to technical reasons. Nevertheless, the artificially produced microemulsions can substitute the plasmatic LDL as carriers for chemotherapeutic agents, since they can also join the LDL receptors, though by means of another protein, the apo E, whereas the LDL joins the receptors by means of the apo D. This hypothesis has been confirmed in patients with acute myeloid leukemia (AML), a disease in which the LDL receptors are 3 to 100 times increased. In this group, the plasmatic removal of the microemulsions, marked with a radioactive cholesterol ester, was much faster than when ejected in normal individuals, or in individuals with acute lymphocytic leukemia, a disease in which the expression of the receptors is normal. When the AML patients were treated, achieving the remission of the disease, a condition in which the cells with exceeding LDL receptors disappear, the plasmatic removal of the microemulsions normalized, clearly showing that the microemulsions have the capacity of specific penetration into the neoplastic cells. Anticancer drugs, mainly those of hydrophobic nature, can thus be incorporated to the microemulsions, which conduct said drugs to the cancerous cells, minimally affecting the normal tissues, thereby highly reducing the toxic aggression of the chemotherapeutlc agent. This occurs whenever the cancer lineage has an increased expression of the LDL receptors, as already described in the literature relative to acute myeloid leukemia, myeloproliferous diseases, glioma, endometrial carcinoma, carcinoma of the prostate, uterine carcinoma, cancer of the breast, cancer of the gall bladder and cancer of the lung. Due to their high affinity for the receptors, the microemulsions marked with radioactivity or other means, can also be useful for diagnostical purposes or for localizing malignant tumors. The microemulsions marked, for example, with 99 m Tc-perteclmtate radioisotopes, were capable of generating nuclear medicine images of solid tumors, such as mammary carcinoma, carcinoma of the gall bladder, etc.

What we discovered was not howto make the microemulsion (this is described in the literature, see below for some references), but that microemulsions without protein can interact with the LDL specific receptors, the so-called B, E receptors. We discovered that the non-protein microemulsion, when injected into the plasma compartment, by collision with the native lipoproteins, acquire apolipoprotein E, which is present on the surface of native VLDL (very low density lipoprotein) or HDL (high-density lipoprotein). We observed that the receptor recognizes apo E bound to the microemulsion, and this allows the artificial particles to be sequestered into the cells (by receptor-mediated endocytosis). As several lineages of neoplastic cells have a very increased number of LDL receptors (this was also described in the literature, and the increase can be up to 100 times compared to normal cells), they can swallow great amounts of microemulsion particles. Meanwhile, normal cells have nearly "closed gates" for the entry of the artificial particles. The laws of physical chemistry allow incorporation of hydrophobic lipophilic substances to the hydrophobic core, of the microemulsion.

Incorporation of these drugs do not diminish the capacity of the microemulsion to incorporate apo E in the plasma and bind to the receptors. In human subjects, we observed no change in the plasma kinetics of the radioactively labeled microemulsion when carmustine or cytosine-arabinoside were associated to it, which confirms the statement above. Any chemotherapic agent that is lipophilic or can be reversed to lipophilic can be associated with the microemulsions. The microemulsion mimics lipoproteins, which are present in the plasma circulation. Thus, they are atoxic for the olrganism. We can estimate that many grams of the microemulsion can be infused into the bloodstream, diluted, e.g., in a saline buffer. The concentration of apo E in the plasma is enough to bind many grams of the microemulsion and internalize the article;particles into the neoplastic cells within periods of 10–20 hours. Grossly, it can be estimated that up to 20–25% of a hydrophobic anti-cancer agent can be associated to the core of the artificial particles. Future studies are necessary to determine the efficacy and toxicity of each drug that is incorporated to the emulsion, since, association with the emulsion modifies the biodistribution of drugs, which tend to follow the biodistribution of the microemulsion. The amount of microemulsions and associated drug necessary for cancer treatment will depend upon the drug and the specific neoplastic disease, to be established in future studies.

Preparation of lipid microemulsions without containing protein is described in the literature (Ginsburg, Atkinson & Small, J. Biol. Chem. 257:8216, 1982 Atkinson & Redinger, J. Lipid Res. 31:849 1990, and others). However triglycerides like triolein can also be used. The inclusion of hydrophobic drugs, e.g. carmustine, cytosine arabinoside, to form the emulsiondrug complex is made after the microemulsion is already prepared, by co-sonicating the microemulsion with the drug for one minute or by simple incubation. The final composition of the emulsion we studied was 64% phospholipids, 33% cholesterol oleate, 1% unesterified cholesterol and 2% triolein. All the procedure under sterile conditions to avoid pyrogens. The microemulsion was made from a mixture of 40 mg phosphatidylcholine, 20 mg cholesterol oleate, 1 mg triolein and 0.5 mg unesterified cholesterol. Saline buffer was added to this mixture, which were sonicated for one hour with delivery of 70–80 watts, the temperature maintained around 50–54 C.

The resulting emulsion was purified by ultracentrifugation as described in the papers mentioned above, dialyzed and filtered for sterilzation in an injection in human subjects. We incorporated the drug carmustine up to 15% of the total weight. The composition of the emulsion can be modified for better incorporation of the chemotherapics, since a variety of those agents can be complexed with the emulsion. For instance the percentage of triolein can be increased to 20% to allow the formation of a bigger microemulsion particle that will be able to carry a greater amount of the drug per particle. The point is that many variations of the microemulsion we studied can do the same job, i.e., when injected into plasma associate with apo E, bind to the LDL receptors and be internalized preferentially in neoplastic cells that have over expression of those receptors, and for this mechanisms carry anticancer drugs specifically of those cells.

What is claimed is:

1. A method for treating neoplasms, wherein cells from said neoplasms have an increased number of LDL receptors compared to normal cells, comprising:

binding apolipoprotein E in the blood plasma to a surface of a microemulsion comprising a nucleus of cholesterol esters and no more than 20% triglycerides surrounded by a core of phospholipids and free cholesterol and containing a chemotherapeutic drug, wherein the surface of said microemulsion consists essentially of the particles of a lipidic mixture;

binding the apolipoprotein E to the LDL receptors on the neoplastic cells; and delivering the drug to said neoplastic cells.

2. The method of claim 1, wherein said neoplasms to be treated are acute myeloid leukemia, myeloproliferous diseases, glioma, endometrial carcinoma, prostate carcinoma, uterine carcinoma, breast cancer, gall bladder cancer or lung cancer.

3. The method of claim 1, wherein said chemotherapeutic drug is hydrophobic.

4. The method of claim 3, wherein said chemotherapeutic drug is carmustine or cytosine arabinoside.

* * * * *

UNITED STATES PATENT AND TRADEMARK OFFICE
CERTIFICATE OF CORRECTION

PATENT NO. : 5,578,583
DATED : November 26, 1996
INVENTOR(S) : Raul C. MARANHÃO

It is certified that error appears in the above-indentified patent and that said Letters Patent is hereby corrected as shown below:

On the title page: Item [30] please add the following:

Foreign Application Priority Data

Apr. 2, 1992   [BR]   Brazil ............. PI 9201168--.

Signed and Sealed this

Eighth Day of April, 1997

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,578,583

DATED : November 26, 1996

INVENTOR(S) : Raul Cavalcante MARANHAO

It is certified that error appears in the above-identified patent and that said Letters Patent is hereby corrected as shown below:

On the title page, item [73]

Delete "Fundacão E. J. Zerbini" and insert therefor -- Fundação E. J. Zerbini --

Signed and Sealed this

Fourteenth Day of March, 2000

Attest:

Q. TODD DICKINSON

Attesting Officer

Commissioner of Patents and Trademarks